United States Patent [19]
Lloyd et al.

[11] Patent Number: 5,462,748
[45] Date of Patent: * Oct. 31, 1995

[54] BIOPOLYMER SYNTHESIS APPARATUS AND METHOD

[75] Inventors: David H. Lloyd, Daly City; Robert J. DeFranco, San Carlos; Charles S. Ladd, Union City, all of Calif.

[73] Assignee: Applied Biosystems, Inc., Foster City, Calif.

[*] Notice: The portion of the term of this patent subsequent to Mar. 29, 2011, has been disclaimed.

[21] Appl. No.: 183,104

[22] Filed: Jan. 14, 1994

Related U.S. Application Data

[63] Continuation of Ser. No. 883,541, May 15, 1992, abandoned, which is a continuation-in-part of Ser. No. 788,322, Nov. 5, 1991, Pat. No. 5,298,259.

[51] Int. Cl.$^6$ ............................. A61K 9/10; A61K 9/16; C07K 1/06; C07K 1/10; B65D 3/26; B01J 19/18
[52] U.S. Cl. .......................... 424/484; 424/486; 424/501; 935/88; 422/82.02; 422/64
[58] Field of Search ...................................... 424/484, 486, 424/501; 935/88, 87; 422/82.02, 64, 62, 81, 101, 102, 105, 119, 132, 134, 189, 208, 255, 292, 296, 297; 435/289, 313; 436/55

[56] References Cited

U.S. PATENT DOCUMENTS

| | | | |
|---|---|---|---|
| 3,959,569 | 5/1976 | Burkholder, Jr. | 117/16 |
| 4,059,406 | 11/1977 | Fleet | 422/82.02 |
| 4,746,490 | 5/1988 | Saneii | 935/87 |
| 4,783,335 | 11/1988 | Lipshitz | 424/407 |
| 4,816,513 | 3/1989 | Bridgham | 525/54.11 |
| 4,861,866 | 8/1989 | Durrum et al. | 530/333 |
| 5,001,417 | 3/1991 | Pumphrey et al. | 422/64 |

OTHER PUBLICATIONS

Graham, N. B. and McNeill, M. E., "Hydrogels for controlled drug delivery," Biomaterials 5:27–36 (1984).

Narang, S. A., et al., "Improved Phosphotriester Method for the Synthesis of Gene Fragments," Methods Enzymol. 68:90–98 (1979).

Primary Examiner—Edward J. Webman
Attorney, Agent, or Firm—Peter J. Dehlinger; Vincent M. Powers

[57] ABSTRACT

A cartridge containing a dry polymer composition carrying trapped biopolymer subunits for use in synthesis of biopolymer chains provides a discrete unit for stepwise supply of subunits, such as protected amino acids, in an automated apparatus for biopolymer synthesis. The composition is swellable in organic solvent to release and supply the subunits to a growing biopolymer chain immobilized on a polymer support. An automated synthesizer uses the cartridges for sequential subunit supply and monitors conductivity of deprotection reagents to control cycling and timing of steps.

12 Claims, 7 Drawing Sheets

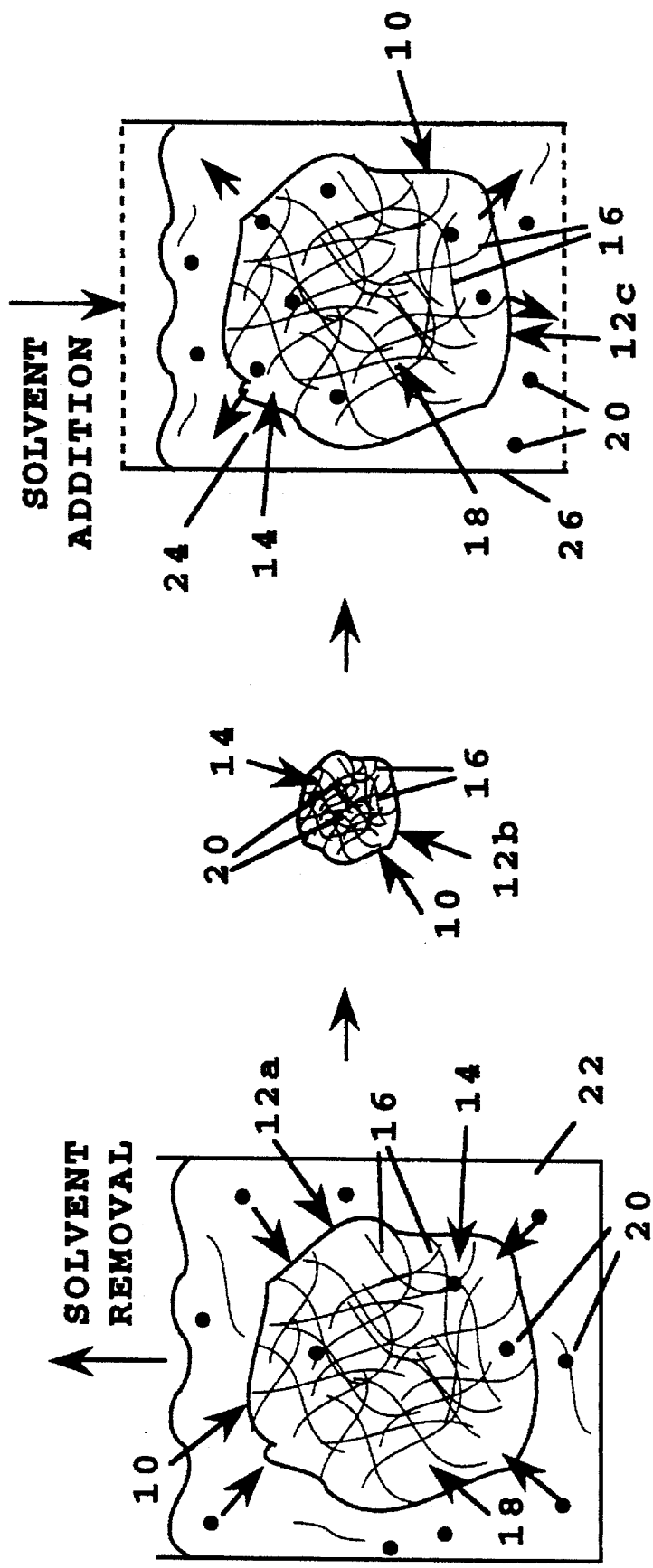

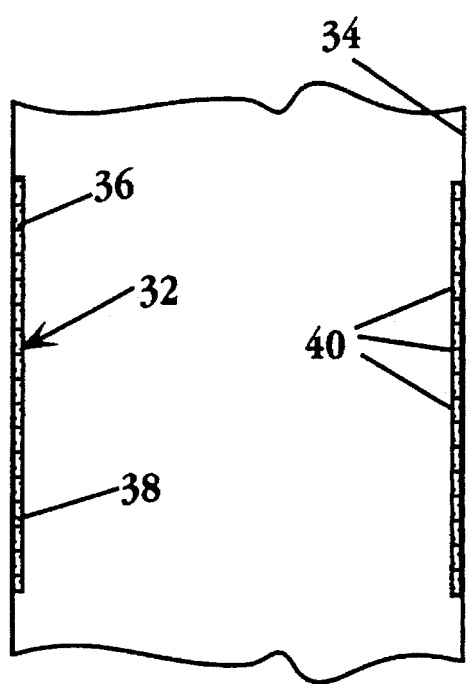
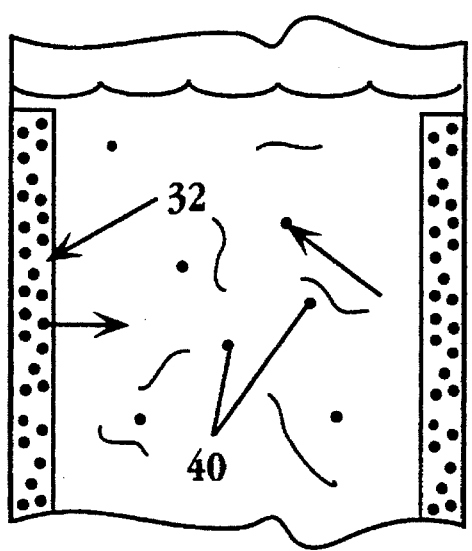
Fig. 2A                Fig. 2B
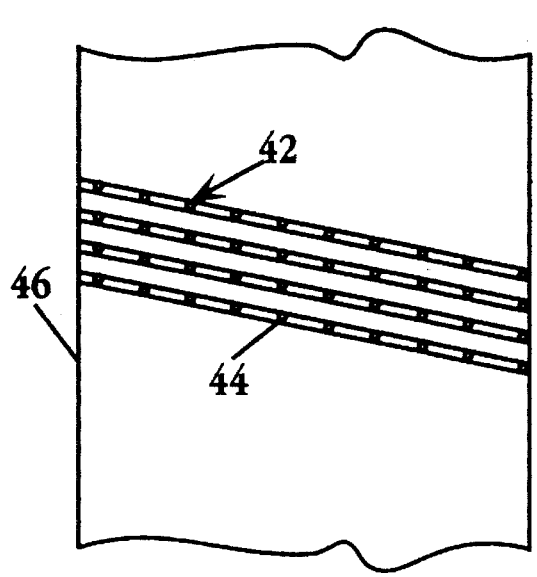
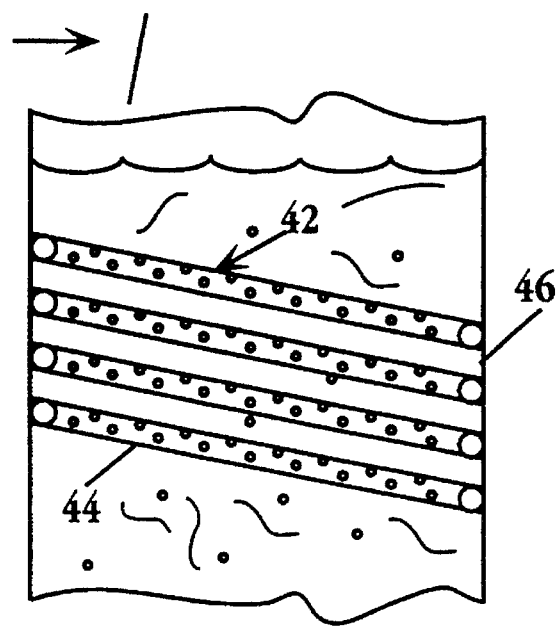
Fig. 3A                Fig. 3B

1

BIOPOLYMER SYNTHESIS APPARATUS AND METHOD

This application is a continuation application under 37 CFR 1.62 of prior application Ser. No. 07/883,541, abandoned, filed on May 15, 1992 entitled BIOPOLYMER SYNTHESIS APPARATUS AND METHOD, which is in turn a continuation-in-part of application Ser. No. 07/788,322 filed Nov. 05, 1991, U.S. Pat. No. 5,298,259.

FIELD OF THE INVENTION

The present invention relates to instruments and methods for synthesis of biopolymers, and in particular, to automated apparatus and methods for such synthesis.

BACKGROUND OF THE INVENTION

Selected-sequence biopolymers, such as polypeptides and polynucleotides, are routinely synthesized by solid-phase methods in which a series of selected polymer subunits are added sequentially to a growing polymer chain carried on a solid support. In a typical polypeptide synthesis, the polymer is synthesized stepwise from an immobilized C-terminal residue. At each step, a new N-protected amino acid is added in solution to the solid support, and reacted through its free carboxyl group with the free α-amine group of the amino acid (or peptide) immobilized on the support, to couple the new amino acid to the growing peptide on the support. The support is then treated to remove the N-protecting group of the last added amino acid, and the procedure is repeated in a stepwise fashion until the final polypeptide is complete.

A polynucleotide, e.g., DNA strand, is similarly synthesized by solid-phase methods, by stepwise addition of a selected 5'-protected nucleotide to a resin containing an immobilized 3'-end nucleoside. Backbone coupling is between the free 5' OH group of the immobilized nucleoside, and the activated 3'-end of the free nucleotide. After the coupling reaction, the support is treated to remove the 5'-end protecting group, and the reaction steps are repeated stepwise until the desired-sequence polynucleotide is complete.

Solid-phase methods for polypeptide and polynucleotide synthesis can be carried out conveniently by automated synthesizers which are designed for successive addition of selected subunits, coupling agents, and deprotecting agents to a vessel containing the solid-phase material. That is, each subunit addition step involves (a) adding a deprotection solution to the solid-phase vessel, to deprotect the last-added residue on the immobilized support, and (b) adding the next subunit, either in activated form or in the presence of an activator, to the solid-phase vessel, to couple the subunit to the growing polymer chain on the solid support.

In a typical operation of an automated synthesizer, the machine is first loaded with vials containing each of the subunits which are to be added during operation, and with the deprotection and wash solutions used during operation. The vials containing the individual subunits may be pre-packaged in liquid form, allowing the subunit solution to be transferred readily from the vial to the solid-phase vessel. Such vials, of course, must be stored in a manner which prevents leakage or breakdown of the subunit or activation components.

Alternatively, the vials may be packaged in dried form. The dried material is either manually dissolved prior to loading into the machine, or more commonly, is dissolved during machine operation, by addition of a selected volume of solvent to each vial. One limitation of the dried material is that, for many amino acids, a low bulk density of the material makes the material difficult to measure and package. In addition, some dried amino acids dissolve very slowly and may require up to thirty minutes of contact time with an added solvent before the subunit is fully dissolved. For these reasons, a composition having handling and dissolution properties which are superior to those of the existing available reagents would be useful.

Automated apparatus has been built for synthesis of polypeptides and polynucleotides as described above, but there are many problems that have never been adequately overcome. Among them are a need for ease of use, relatively low instrument cost, and low cycle costs.

The need for ease-of-use relates to a developing market in which users of synthesizers are not experienced peptide and polynucleotide chemists, but increasingly are immunologists, neurobiologists, and molecular biologists, among other disciplines. Lacking the particular experience of peptide chemists, these new users need relatively more automatic and trouble-free operation than has been previously provided.

There is also a perceived need for a relatively small scale instrument, capable of ordering the synthesis of chains of thirty subunits or so, adequate for most requirements of the new class of users. At the same time, since the use of such an instrument may not be as extensive as it might be for an instrument in a research lab devoted to full-time preparation of macromolecules by peptide and polynucleotide chemists, there is a greater need for low initial cost, and certainly a greater need for low cycle costs. The cycle costs are the costs for subunit materials, reagents, and the like, used in the synthesis operations.

Another need not yet adequately met, that relates to the use of such an instrument by researchers not particularly experienced in peptide and polynucleotide synthesis, is the need for monitoring the reactions involved. It is known, for example, that coupling reactions are sometimes unexpectedly slow, and it has been observed that slow coupling reactions in peptide synthesis are often preceded by slow deprotection steps.

What is needed then, in addition to a composition for subunit materials having handling and dissolution properties which are superior to those of existing available reagents, is a relatively low-cost, very reliable instrument capable of synthesizing molecules of moderate length (30 subunits or so), with monitoring capability coupled with automatic adjustment of timing for coupling steps. In addition the instrument needs to be very reliable and easy to use.

SUMMARY OF THE INVENTION

In one aspect, the invention includes a polymer composition comprising a dried polymer substrate which is swellable, but insoluble, in an organic solvent and which has an internal polymer matrix. Biopolymer subunit molecules are entrapped within the polymer matrix of the substrate. When the substrate is swelled by contact with an organic solvent, the subunit molecules diffuse out of the matrix into the swelling solvent.

The polymer substrate may be formed of polystyrene, polyacrylate, polymethacrylate, polyacrylamide, polyvinylpyrrolidone, or co-polymers thereof, and the polymers are crosslinked with a suitable cross-linking reagent, preferably having a concentration of between 0.5 and 5.0 mole percent. The substrate is preferably capable of swelling in the presence of an organic solvent to a volume which is at least 5–10 times that of the its dry volume.

In one preferred embodiment, the substrate comprises particles which form a flowable mass in a dried state. A preferred particle polymer is polystyrene crosslinked with 1.0% divinylbenzene. The polymer particles preferably contain entrapped biopolymer subunit molecules at a weight ratio of biopolymer subunit to polymer of about 1:10 to 2:1, and the particles containing entrapped biopolymer subunit have a density between about 0.5 and 0.6 g/cc.

In one embodiment, for use in an automated polypeptide synthesizer, the biopolymer subunit in the composition is an N-protected amino acid. In another embodiment, for use in an automated polynucleotide synthesizer, the biopolymer subunit in the composition is an activated, 5'-OH protected nucleotide.

In another aspect, the invention includes a cartridge for use in an automated solid-phase synthesis apparatus. The cartridge includes a chamber which contains the polymer composition of the type just described. The cartridge also includes ports for solvent addition and removal, during operation.

In yet another aspect, the invention includes an automated method for solid-phase synthesis of a biopolymer by a sequential addition of a biopolymer subunit to a growing biopolymer chain carried on a solid-phase support. The method includes placing in a position for fluid transfer, a subunit delivery cartridge of the type described above, and adding an organic solvent to the cartridge, to cause the polymer substrate in the cartridge chamber to swell and release said biopolymer subunit into the solvent to form a solution of the subunit. The solution is then transferred into a reaction vessel containing the solid-phase support.

In another aspect, the invention includes an automated system for solid-phase synthesis of a biopolymer by a sequential addition of a biopolymer subunit to a growing biopolymer chain carried on a solid-phase support. The system includes a plurality of cartridges, like the one described above, and an automated synthesis apparatus which includes the elements: (i) a cartridge holder adapted to hold the cartridges; (ii) fittings movable to a position effective to engage the openings in a selected cartridge in the holder, forming a fluid-tight seal with the cartridge's openings; (iii) a mechanism for placing a selected cartridge in said holder to a transfer position at which the engaging means is engageable with the opening means of the selected cartridge; (iv) a reaction vessel for containing such solid-phase support; and (v) a fluid-transfer assembly for transferring organic solvent into the chamber of such a selected cartridge, and for transferring solution out of the chamber into the reaction vessel.

These and other objects and features of the invention will become more fully apparent when the following detailed description of the invention is read in conjunction with the accompanying drawings.

BRIEF DESCRIPTION OF THE DRAWINGS

FIGS. 1A–1C are schematic illustrations of a composition particle (1A) during formation by subunit influx and solvent removal, (1B) in a dried, storage state, and (1C) during swelling and release of entrapped subunit (1C);

FIGS. 2A and 2B are schematic illustrations of a composition formed in accordance with another embodiment of the invention, shown before and after swelling by solvent addition;

FIGS. 3A and 3B are schematic illustrations of a composition formed in accordance with another embodiment of the invention, shown before and after swelling by solvent addition;

DESCRIPTION OF THE PREFERRED EMBODIMENTS

A. Polymer Composition

Figure 4:
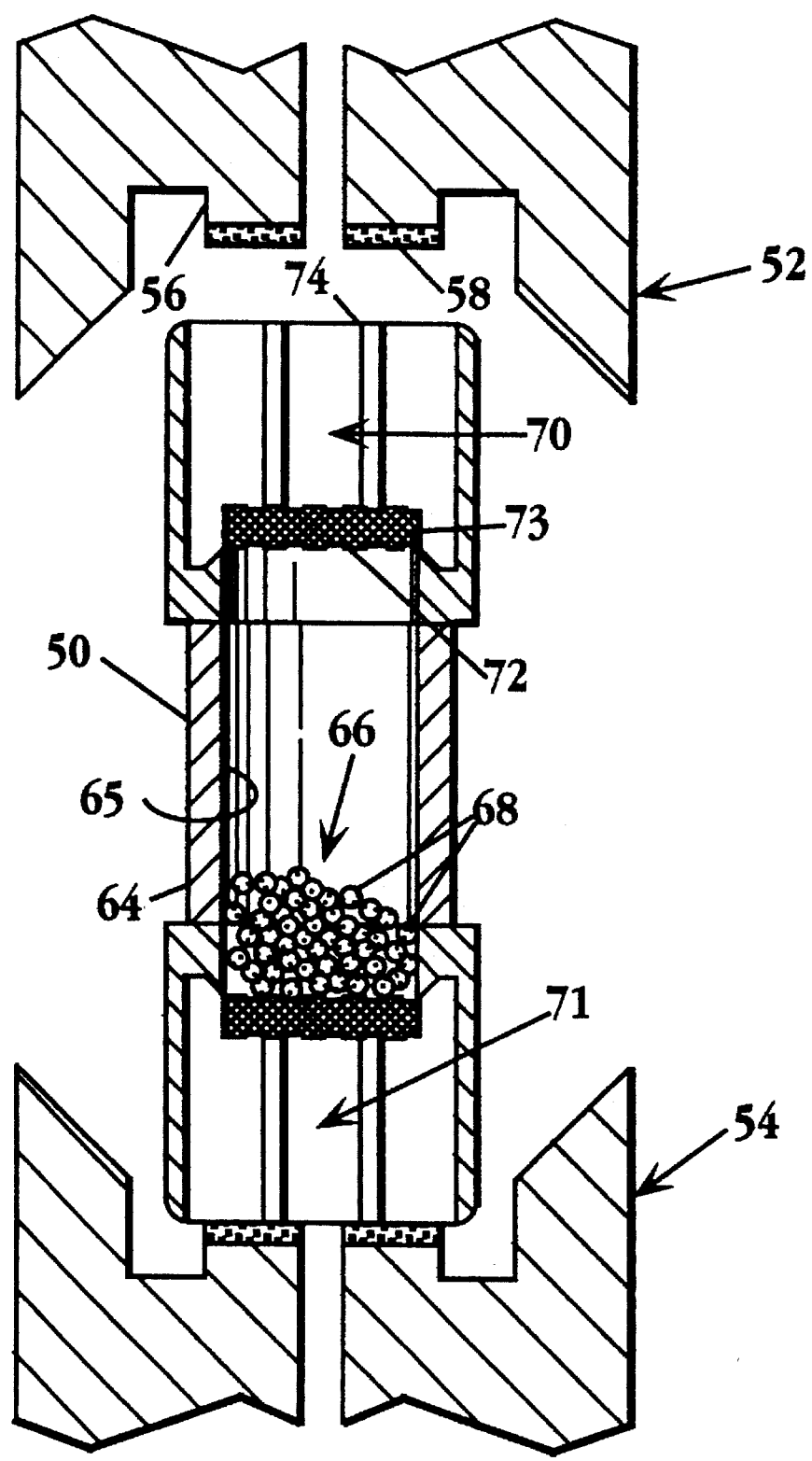
FIG. 4 shows a cartridge constructed according to the invention, containing a dried polymer particulate composition, such as shown at FIG. 1B.

The composition of the invention is designed as a storage form of a biopolymer subunit, for use in supplying a given amount of the subunit in solution form in an automated biopolymer synthesis apparatus.

The composition is indicated generally at 10 in FIGS. 1A–1C, which show a particle, indicated at 12a, 12b, and 12c in FIGS. 1A–1C, respectively, of the composition. The particle is formed of a polymer substrate 14 which is swellable in a selected organic solvent, such as N-methylpyrrolidone (NMP), dimethyl formamide (DMF), dichloromethane (methylene chloride), or chloroform, which is suitable for solid-phase subunit addition reactions in biopolymer synthesis. The substrate is formed of cross-linked polymer filaments, such as filaments 16, which form a matrix 18 through which biopolymer subunit molecules, such as subunit molecules 20, can freely diffuse when the substrate is in a swollen state.

A variety of polymers are suitable for use in the invention. These include polystyrene, polyacrylate, polymethacrylate, polyacrylamide, polyvinylpyrrolidone, as well as co-polymers thereof. The polymers are lightly cross-linked by inclusion of a crosslinking agent in the polymer composition, preferably at a mole percent of about 0.5–5. One preferred polymeric composition consists of polystyrene cross-linked with of 1% divinylbenzene.

More generally, any polymer which, in a cross-linked matrix, is swellable and insoluble in solvents such as DMF, methylene chloride, or chloroform used in solid-phase biopolymer synthesis, and which allows for subunit diffusion through the polymer matrix, in a swollen-substrate state, is suitable. Preferably the swollen volume of the polymer (in the swelling solvent) is at least 5–10 times its dried volume.

Polymeric particles which are used in forming the composition serve to increase the overall bulk density and thereby improve flow properties of the dried biopolymer subunit reagent, so that a preweighed amount of the subunit can be more easily loaded into a vial. One preferred form of the substrate is polymer beads, preferably having diameter size range of a diameter of at least 50 microns, and preferably within the range of 75–200 microns, in dried form. Polystyrene beads having the desired polymer composition, swellability, and particle size, in dried form, are commercially available from Eastman Kodak, Biorad, or Polymer Lab.

FIG. 1A illustrates a method of preparing the composition, i.e., loading the substrate with the biopolymer subunits. A solution of the subunits in a suitable solvent 22, such as one of the organic solvents mentioned above, is mixed with the polymer particles in a mixing vessel. The concentration of particles is such as to form a particle slurry, which may be relatively viscous after the particles have swelled. The concentration of polymer subunits in the solution is selected to produce a final desired weight ratio of subunit/dried substrate preferably between about 1:10 to 2:1. For use with an automated polypeptide synthesizer, the biopolymer subunits are preferably N-protected amino acids, typically one of the 20 natural L-acids having protected alpha-amine groups, and protected carboxy, hydroxy, thiol, and amine side chain groups. For use with an automated polynucleotide synthesizer, the subunits are typically activated 5'-protected nucleotides, such as one of the four DNA deoxynucleoside 3'-phosphoramidites having a 5' dimethoxytrityl (DMT) blocking group.

During formation of the composition, the subunit molecules infiltrate the matrices of the swollen particles, as they equilibrate between the bulk phase of the suspension and the entrapped matrix volume. At the same time solvent is removed from the particles, forcing progressively more of the subunit molecules into the entrapped volume. Solvent removal is carried out, with agitation, until the particles are completely dried, and substantially all of the subunit is entrapped (or associated with) the particles.

FIG. 1B illustrates a dried particle 12b in the composition, after complete solvent removal. As noted above, particle size in the dried state is preferably between about 50 and 200 microns, and several times less than that in the swollen state. The dried particles have a known amount of subunit per composition weight, and form a flowable particle composition which can be readily transferred, in known weight amounts, from one vessel to another. The preparation of a particle composition containing entrapped Fmoc protected L-(amino acid) is detailed in Example 1.

FIG. 1C illustrates how the particles in the composition are used in forming a solution of biopolymer subunit molecules, in an automated synthesizer operation. Here a suitable solvent, such as solvent 24, is added to a vial 26 containing the loaded particles, such as particle 12c. As the particles swell in the solvent, the subunits entrapped in the particle matrices, such as subunits 20, diffuse out into the solvent. At final equilibrium, the concentration of subunits in the bulk phase medium in the vial is equal to that in the entrapped matrix. Preferably, the volume of the swelled resin represents no more than approximately 20–50%, and more preferably, no more than about 5–20%, of the total volume of the solvent in the extraction system. This insures that at equilibrium, the bulk phase medium will contain at least about 50–80%, and more preferably, at least about 80–95%, of the total extractable biopolymer subunit molecules. Therefore, at least about 50–80% of the subunit present in the dried composition, and more preferably at least about 80–95%, is recovered in the bulk phase medium.

In a typical automated polypeptide synthesis operation, the composition in the vial is designed to supply about 0.075 mmole amino acid in about 1 ml bulk-phase solution. In a typical automated polynucleotide synthesis operation, the composition in the vial is designed to supply about 1 μmoles activated nucleotide in 0.5 ml bulk-phase solution.

Solvents which are suitable for the swelling and extraction step just described include solvents which facilitate swelling without dissolving the polymer particles and which are compatible with the synthetic reaction in which the biopolymer subunit is to participate. In one embodiment in which N-α-protected amino acids are added to a peptide synthesis reaction utilizing 9-fluorenylmethoxycarbonyl (Fmoc) chemistry, a useful solvent is dimethylformamide (DMF). Activating agents compatible with polypeptide reaction may be added to the polymer composition with the solvent. Alternatively, or in addition, amino acids can be added in activated forms, such as symmetrical anhydrides, pentafluorophenyl esters and 1-oxo-2-hydroxydihydrobenzotriazine active esters.

An activating agent which can be used in the aforementioned Fmoc based peptide synthesis is hydroxy-O-benzotriazole, tetramethyluronium hexafluorophosphate (HBTU), to which is added an equivalent amount of hydroxy-O-benzotriazole (HOBT), and 2 equivalents of diisopropylethylamine (DIEA). Another appropriate solvent/activator solution is dichloromethane (DCM)/dicyclohexyl carbodiimide (DCC) for tertiary-butyloxycarbonyl (t-Boc) based peptide synthesis. A solvent system appropriate for the above-mentioned HBTU/HOBT/DIEA activator system is dimethylformamide (DMF)/N-methyl-pyrrolidone (NMP)/dimethyl sulfoxide (DMSO) for Fmoc based peptide synthesis. Other solvent/activator combinations are also possible, and optimal combinations for a given synthetic reaction depend on the type of synthesis and the type of chemical coupling system used in the synthesis.

In a particle composition formed from the abovedescribed polystyrene beads, and containing selected 5'-OH DMT-protected, 3' phosphoramidite deoxribonucleoside subunit, a useful solvent is acetonitrile. Other appropriate solvents are methylene chloride, and acetonitrile/methylene chloride mixtures.

In a particle composition having a weight ratio of L-amino acid:polymer of 1:2, the time required for equilibration of amino acid into bulk phase for 50 mg of composition suspended in 1 ml DMF is between about 1 and 5 minutes at room temperature, depending on the particular amino acid and polymer material. After equilibration, the bulk phase medium is removed from the vial, preferably through a filtration medium, for use in a subunit addition reaction in an automated synthesizer, as described below.

FIGS. 2A and 2B illustrate a composition 32 formed in accordance with another embodiment of the invention. In this embodiment, the composition has a film-like polymer substrate 36 which forms a lining or coating 38 on the sides of a vial 34. The substrate contains entrapped subunit molecules, such as molecules 40, and has a polymer composition similar to that of composition 10 described above. The substrate lining has a thickness, in dried form, preferably between about 25–100 microns. The substrate is loaded with a selected amount of subunit, as above, by solvent removal from a solution of the subunit in a solvent capable of swelling the polymer.

FIG. 2B illustrates the condition of composition 32 during subunit release, when a suitable reaction solvent 40 is added to the vial. As the substrate swells in the added solvent, the entrapped subunit diffuses through the substrate matrix and into the bulk-phase medium, until equilibrium is achieved. The resulting subunit solution is then drawn off for use in a subunit addition reaction.

FIGS. 3A and 3B illustrate a composition 42 formed in accordance with a third embodiment of the invention. In this embodiment, the composition has a filament-like substrate 44, which may be attached to the walls of a vial 46, as indicated. The substrate, which contains entrapped subunit molecules, has a polymer composition similar to that described above. The filament thickness, in dried form is preferably between about 25–200 microns. The substrate is loaded with subunit molecules as above. FIG. 3B illustrates the composition after substrate swelling and subunit release, for use in preparing a subunit solution for solid-phase biopolymer synthesis.

B. Cartridge

In another aspect, the invention includes a cartridge for use in an automated solid-phase synthesis apparatus, for delivering a selected amount of biopolymer subunit in solution form to a subunit-addition reaction chamber. One exemplary cartridge is shown at 50 in FIG. 4. The cartridge is designed to be engaged automatically by a pair of fittings 52, 54 in the synthesis apparatus, to connect the vial in line with a fluid-transfer assembly in the apparatus, for transferring fluid into and from the cartridge, as discussed below. Fitting 52, which is representative, includes a head 56 having an annular gasket 58 which forms part of a fluid seal, when the fitting is engaged with the cartridge. The seal is formed by moving the two fittings toward one another to positions of sealing engagement with the cartridge. The two fittings are also referred to herein as fitting means.

Cartridge 50 includes a vial or container 64 which defines an internal chamber 65 containing a polymer composition, such described in Section A. In the embodiment shown, the composition is a particle composition 66 composed of dried polymer particles, such as particles 68. It will be appreciated that other polymer compositions, such as the film- or filament-type compositions described above, are also suitable. A typical cartridge has a container volume of about 0.5 ml, and contains about an amount of subunit corresponding to about 0.075 mmoles of amino acid subunit, or about 1 µmoles of activated polynucleotide. The container is preferably formed of polyethylene or similar resilient plastic.

The cartridge is provided with inlet and outlet ports, or port means, 70, 71 through which solvent is introduced into and removed from the cartridge, respectively. Inlet port 70, which is representative, is formed by a central opening 72 in an end of the container, covered by a porous membrane 73 which is effective to filter particles, in either dried or swelled form, as solvent is passed through the filter. Each end of the vial, such as the end confronting fitting 52, is provided with an annular ridge, such as ridge 74, which meshes with the annular gasket of the confronting fitting, to form a fluid-tight seal, when the fitting is moved into sealing position.

It will be appreciated that a film- or filament-type composition which is anchored to the vial walls may not require a filter membrane to contain the composition within the vial before and after swelling. Further, the port means may include a single port for receiving a fitting that serves both to supply and remove solvent from the container.

C. Automated Biopolymer Synthesizer

Figure 5:
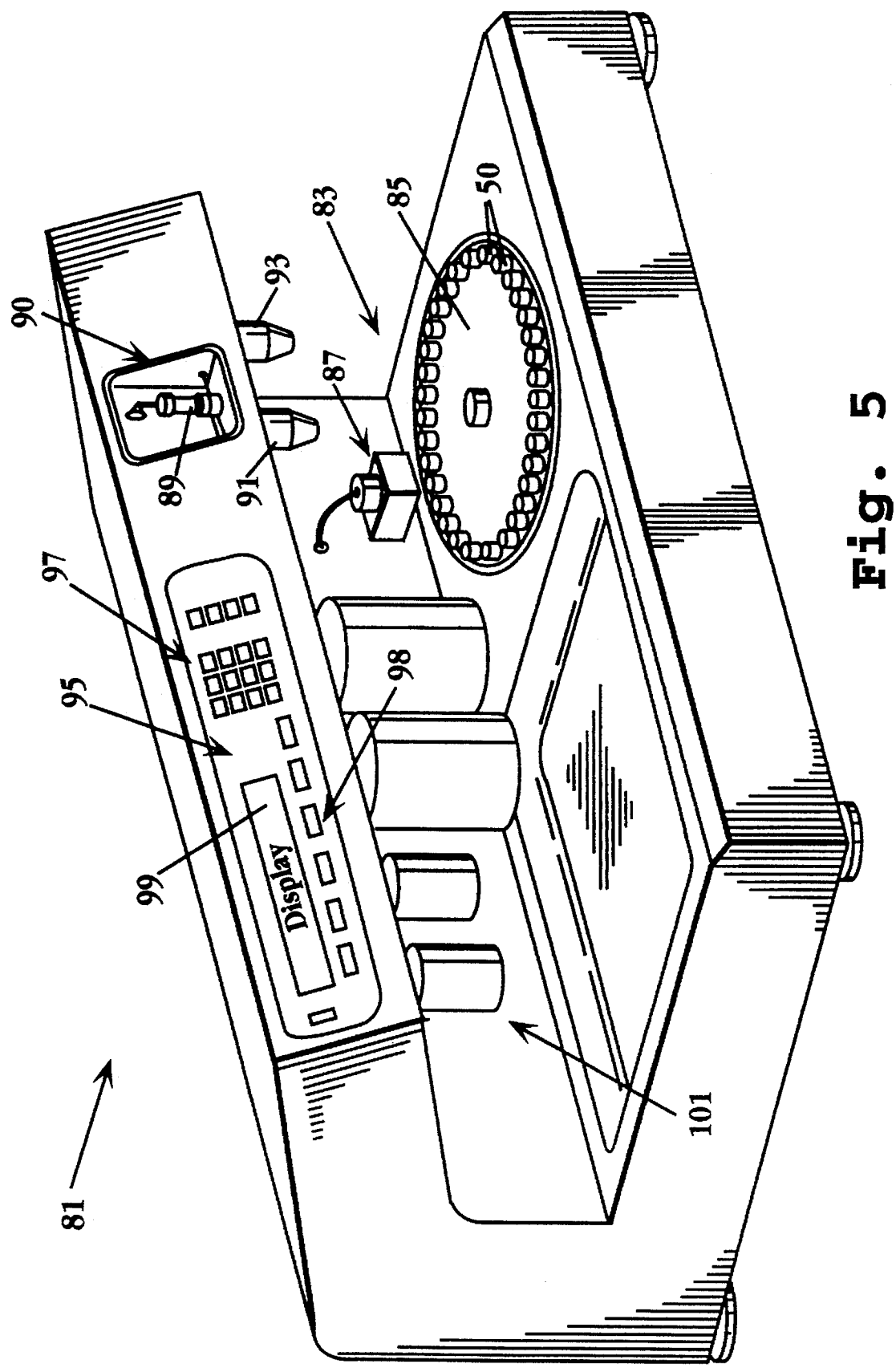
FIG. 5 shows a synthesizer apparatus according to the invention.

FIG. 5 is an orthographic view of an automated biopolymer synthesizer or apparatus 81 constructed according to the invention. In a preferred embodiment, synthesizer 81 is used primarily for peptide synthesis. The synthesizer includes a cartridge holder 83 based on a rotary carousel 85 for delivering cartridges of the type described in section B with respect to FIG. 4, with cartridge 50 as an example. The cartridges carry subunit materials in a polymer composition as described in section A above.

The cartridge holder moves through a load station 87 which presents fittings 52 and 54 (FIG. 4) to engage the opposite ends of subunit delivery cartridges so solvent may be flowed through to extract subunit material to be used in the synthesis reaction. Cartridges carrying specific subunits are typically loaded into the carousel in sequential order circumferentially before the synthesis procedure is initiated, then, in operation, the cartridges are delivered to load station 87 in the required sequential order for the desired synthesis.

Solvent flowed through a delivery cartridge on the carousel is conducted to and through a reaction vessel 89 mounted in a recessed area 90. The reaction vessel typically contains (for peptide synthesis) a C-terminal residue on a solid polymer support, as described above. Vessels 91 and 93 are a part of the liquid transfer system, and play a part in efficient and repeatable transfer. The assembly for transferring fluid into or from a cartridge, including fittings 52, 54 which engage the openings of a cartridge, is also referred to herein as fluid transfer means, and includes the transfer structure described in Section D below.

The synthesizer includes a microprocessor-based control system with a control panel 95. The control panel includes input devices, such as a numerical keypad 97 and soft-keys 98 associated with selections displayed on a display 99 for presenting menus to an operator. An area 101 has a variety of vessels for storing and providing various reagents used in the synthesis process. The nature and connection of these vessels is described in further detail in section D below.

D. Transfer Mechanisms and Method

Figure 6:
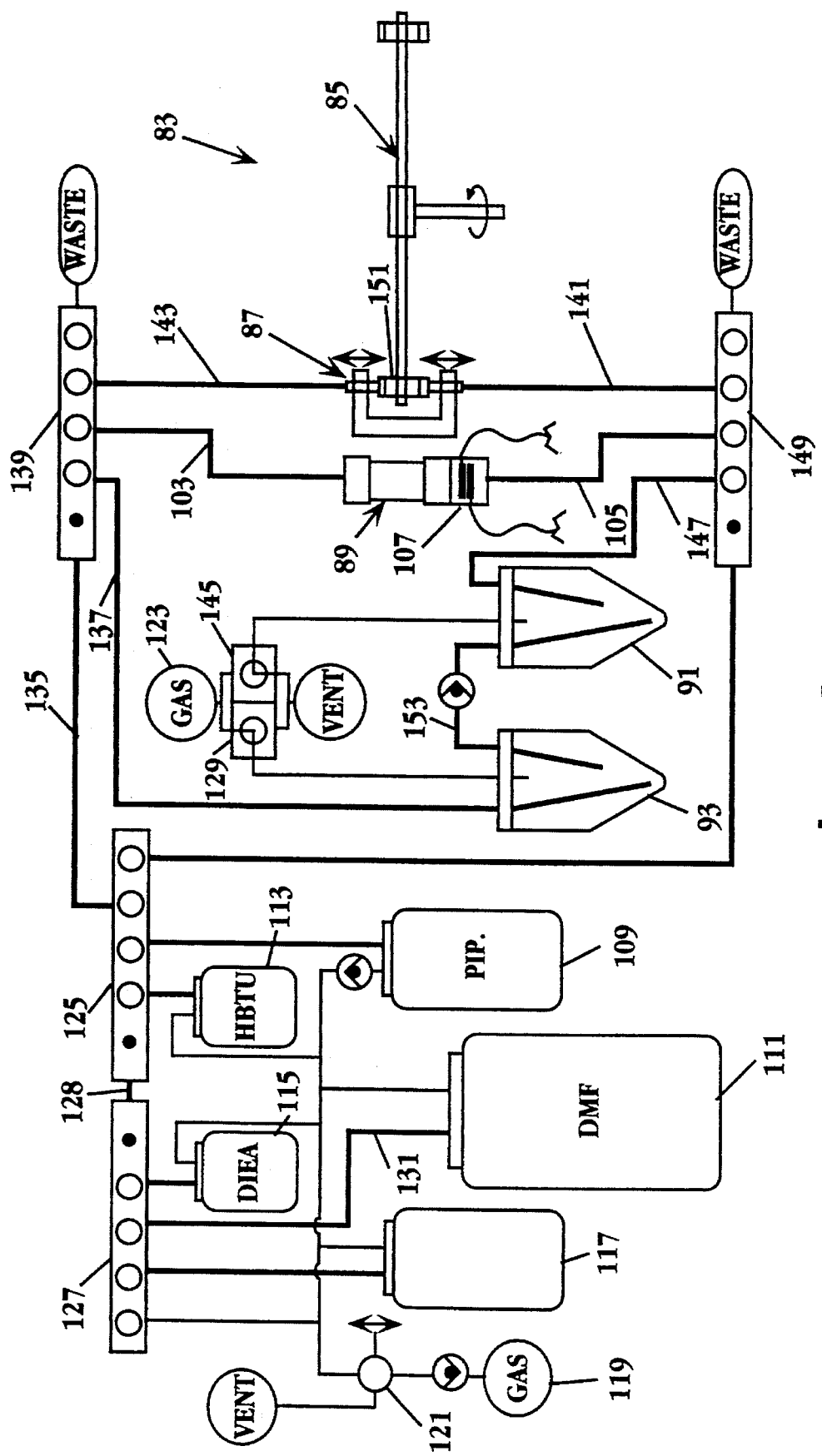
FIG. 6 is a schematic diagram of elements of the synthesizer of FIG. 5 showing particularly fluid delivery systems.

FIG. 6 is a schematic diagram comprising liquid flow conduits, valving, and mechanical presentation of cartridges for the synthesis apparatus depicted in FIG. 5. Operation of the system is described below with reference to FIG. 6, and for peptide synthesis using Fmoc chemistry as an example.

Prior to starting the peptide synthesis of the present example, reaction vessel 89 containing an Fmoc amino acid linked to a polystyrene support is load into the apparatus. The immobilized amino acid is the starting point for the desired peptide chain. A cleavable linker is placed between the C-terminal residue and the polystyrene so the peptide resulting from the sequential synthesis can be removed from the support. For Fmoc synthesis a suitable linker is hydroxymethylphenoxyacetyl (HMPA). The reaction vessel is substantially the same in physical form as the subunit delivery cartridge 50 shown in FIG. 4, having upper and lower openings with suitable filters, and is secured to upper and lower fluid conduits 103 and 105 by means of Luer fittings.

In the flow path immediately below the reaction vessel is a conductivity cell 107 including two gold-coated discs separated by a thin, non-conductive, inert polymer spacer. The discs are connected to electrical leads for applying a potential to test conductivity of solution passing through the cell.

Cartridges containing Fmoc amino acids in the composition described in Part A are placed on carousel 85 in the order circumferentially in which they are desired to be added to accomplish assembly of the desired peptide chain. The circumferential arrangement simplifies the operation of the system in presenting cartridges in the preselected order, but is not required as long as the system is programmed to rotate the carousel to present cartridges with amino acids in the order required for a selected synthesis.

Reagents used in the Fmoc chemistry in the present example include piperidine (Pip.) in vessel 109, dimethylformamide (DMF) in vessel 111, 2-(1H-benzotriazol-1-yl)-1,1,3,3-tetramethyluronium hexafluorophosphate (HBTU) reagent in vessel 113, and diisopropylethylamine (DIEA) in vessel 115. The HBTU reagent in vessel 113 is prepared to contain also an equivalent amount of 1-hydroxy-O-benzotriazole (HOBt). There are other solutions used but not shown in the figure, for such purposes as washing conduits and other elements between transfers, and these are stored in other vessels such as vessel 117 connected to the system.

Each reagent vessel is connected to an inert gas supply 119 through a manually operated valve 121. The gas supply is controlled to about 5 psi in the present example. The vessels are connected to the main fluid lines of the system through solenoid operable valve blocks. As a preparatory step the reagent bottles are filled, sealed and pressurized.

The liquid transfer system of the synthesizer instrument includes vessels 91 and 93, which are used in conjunction with pressurized inert gas supply 123 to transfer reagent mixtures through cartridges on the carousel and through the reaction vessel.

Before a coupling reaction, the Fmoc protection group must be removed (deprotection) to allow addition of the next residue to the growing peptide chain. This is accomplished with a simultaneous delivery of piperidine and DMF flowed through the reaction vessel to waste. Piperidine is thoroughly washed from the system before extracting the next amino acid residue to avoid premature deprotection of the next residue. The Fmoc group is removed in the form of a piperidine-dibenzofulvene adduct.

To begin a coupling reaction, a mixture of HBTU (containing HOBt), DMSO, and NMP, is prepared in vessel 93 by cycling valve functions in valve blocks 125 and 127. To do so, it is necessary to vent vessel 93 through valve 129. For example, conduit 131 may be opened to conduit 128 through valve block 127, conduit 128 to conduit 135 through valve block 125, and conduit 135 to conduit 137 through valve block 139. DMF will then flow from vessel 111 into vessel 93 under the influence of gas pressure supplied from gas supply 119, with vessel 93 vented. The amount of fluid (volume) to flow into vessel 93 is a function of time at the controlled pressure.

In a similar manner DIEA in NMP and DMSO is also flowed into vessel 93 until the required mixture is accomplished. With this exemplary mixture in vessel 93 and a first subunit delivery cartridge 151 at load station 87, translation elements are activated at the load station to extend fittings 52 and 54 (see FIG. 4) which are a part of the load station, to engage subunit delivery cartridge 151 such that fluid may be passed through the cartridge via conduits 143 and 141.

Valve 129 is cycled to connect vessel 93 to gas supply 123, valve 145 is cycled to vent vessel 91, conduit 137 is connected to conduit 143 through valve block 139, and conduit 141 to conduit 147 through valve block 149. Under this condition, the mixture in vessel 93 is transferred from top to bottom through subunit cartridge 151 and into vessel 91. When all of the reagent mixture is transferred, valves are cycled in blocks 139 and 149 to close the flow path through the valve blocks, valve 145 is cycled to pressurize vessel 91, valve 129 is cycled to vent vessel 93, and the reagent mixture is transferred from vessel 91 to vessel 93 through conduit 153. With the reagent mixture in vessel 93 the cycle is complete and may be repeated as needed.

DMF swells the composite in the subunit delivery cartridge, releasing the Fmoc amino acid into the reagent mixture, and the other chemicals activate the amino acid to form a derivative which will readily react with the alpha-amino group of the growing peptide chain (in this case, with the immobilized C-terminal residue in the reaction vessel).

Because one pass through the cartridge may not be sufficient to release and activate all of the subunit amino acid in the composite in the cartridge, several cycles according to the above description are accomplished, with the bulk of the reagent mixture containing the activated amino acid residing finally in vessel 93. Ten to fifteen transfer cycles is typically sufficient. The used cartridge is washed with DMF, followed by a volatile solvent, and gas dried by appropriate cycling of valves before proceeding to the next cartridge. Solvents used for washing, and other waste fluids, are passed via either valve block 139 or 149 to waste containers shown in FIG. 6.

After "extractivation" (extraction and activation), the reagent mixture containing the activated amino acid is flowed through reaction vessel 89 to couple the amino acid subunit to the growing peptide chain. This flow cycle is accomplished in much the same manner as the flow through the subunit delivery cartridge, except valves in valve blocks 139 and 149 are set to connect conduit 137 to conduit 103, and conduit 147 to conduit 105. Again, the flow is from top to bottom.

In the case of flowing the mixture through the reaction vessel, the top to bottom flow is an aid in preventing bubble formation, which would interfere with conductivity monitoring, and also to avoid separating the resin in the reaction chamber, which might introduce unwanted variables. Also, not all of the mixture is transferred in a single cycle from vessel 93 to vessel 91, because to do so would cause the conductivity cell to empty at some point. A single transfer cycle is stopped with a small volume of mixture remaining in vessel 93, then the mixture in vessel 91 is transferred directly to vessel 93, as described above for the extraction operation, before a new transfer cycle is initiated.

Important factors are the degree of swelling of the resin support in the reaction vessel and the concentration of the activated amino acid. Ten to thirty minutes of cycling is typically needed to accomplish coupling, with each cycle being about ten seconds. The actual length of time devoted to a coupling step is determined by monitoring the immediately preceding deprotection step, as is described below in section F titled "Monitoring."

After coupling, the Fmoc protection group must be removed (deprotection) to allow addition of the next residue to the growing peptide chain. This is accomplished with a simultaneous delivery of piperidine and DMF flowed through the reaction vessel to waste. Piperidine is thoroughly washed from the system before extracting the next amino acid residue to avoid premature deprotection of the next residue. The Fmoc group is removed in the form of a piperidine-dibenzofulvene adduct.

The above procedures are repeated for subsequent amino acid residues extracted from the composite in subsequent subunit delivery cartridges until the planned peptide is complete, at which time the reaction vessel is removed from the apparatus, or suitable reagent mixtures may be prepared and flowed through the reaction chamber to cleave the peptide chain from the solid support.

E. System Electronics and Control

Figure 7:
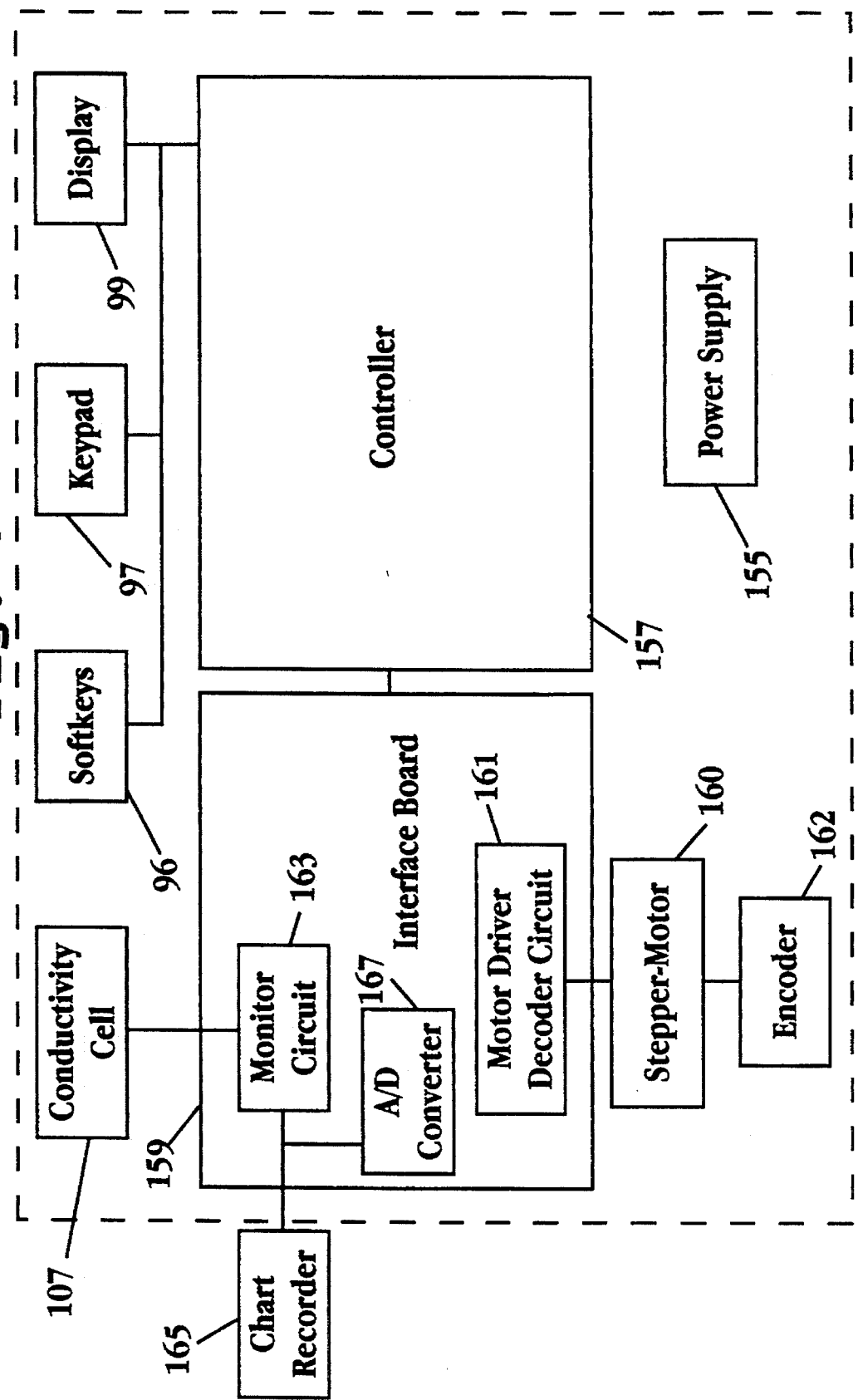
FIG. 7 is a block diagram of power, electronics, and control elements of the synthesizer of FIG. 5.

FIG. 7 is a block diagram of power and control functions for the synthesizer of the invention. Generally control data communication paths are shown between elements, and power connections are not shown, although a power supply 155 is shown as part of the diagram. The power connections are conventional.

Controller 157 is a Motorola 68000-based control board, but could as well be based on other available microprocessors. The controller handles input from keypad 97 and softkeys 98 (see also FIG. 5), and displays menus and other user-directed information on display 99. The controller is coupled to interface board 159 which translates controller output to discrete signals to drive the solenoids for solenoid-operated valves of the synthesizer as well as motor driver and decoder circuitry 161 which drives carousel 85 (FIG. 5 and FIG. 6). The controller sends suitable data to cycle the carousel one cartridge station at a time, and the motor driver circuit provides the required output for stepper motor 160.

An encoder 162 on the carousel feeds back position information to circuitry 161, and hence to the controller.

A monitor circuit 163 is coupled to conductivity cell 107 (see also FIG. 6) to measure conductivity in solution of reagent mixtures passing through the reaction vessel of the synthesizer, and provides output to a chart recorder 165. The monitor output is also provided to an A/D converter 167. The monitoring of the solutions passing through the reaction vessel, and the use of the resulting data is presented in greater detail in section F below.

The software provided with the system has menu-based routines for displaying selections on display 99 which an operator selects by pressing an appropriate softkey from group 98. Some selections present submenus, and some require setup values which an operator enters on keypad 97. There is an automatic mode initiated from the menu system which starts the operation, and controls all the steps necessary to extractivate, couple, and deprotect for amino acids delivered in cartridges on the carousel up to the maximum number of positions on the carousel (in the preferred mode, 30 positions).

There are also setup procedures, shutdown and startup procedures, and manual operating protocols available to an operator. In the automatic mode, there is a unique capability to use the monitor data during operation to control subsequent steps, which is described more fully below in section F devoted to monitoring.

F. Monitoring

Automated peptide assembly is becoming more reliable through advances in solvation and activation chemistry, but the unpredictable "bad" coupling due to a variety of causes continues to be a finite possibility. In solid-phase synthesis, one may either monitor the resin or the reaction solution. Existing instruments often rely on removal of a small resin sample from a reaction vessel for later analysis. Resin analysis is quite reliable, but typically must be done after a synthesis is complete. It therefore offers no potential for "on-line" detection and use in real-time modification of a synthesis operation.

Other ways to monitor are by UV absorbance or by measuring electrical conductivity. In the present invention, with an emphasis on low initial cost for the instrument and low operating costs, conductivity monitoring is the logical choice. The application of conductivity monitoring is best made to deprotection steps, because HBTU solutions present in the coupling reaction are inherently quite conductive.

During deprotection using piperidine a conductive species is released, thought to be piperidinium piperidine carbamate. Conductivity cell 107 (FIG. 6) is supplied with a square wave potential of about 2 V. at about 100 Hz. The current produced is sampled and amplified to produce a DC signal of from about 0 to 2 V. in response to the conductivity of the solution passing through the cell. The signal is recorded on the two pen chart recorder 165 using 0–2 V. range for coupling steps and 0–200 mV range for deprotection steps. The signal is digitized by converter 167.

The digital data from converter 167 is provided to controller 157, averaged over a preset interval, and compared to the previous interval to determine the change in conductance with respect to time, hereinafter $\Delta$. Because the current measured is directly proportional to the conductance, the change in conductance with respect to time is the slope of the trace on the strip chart recorder.

Figure 8:
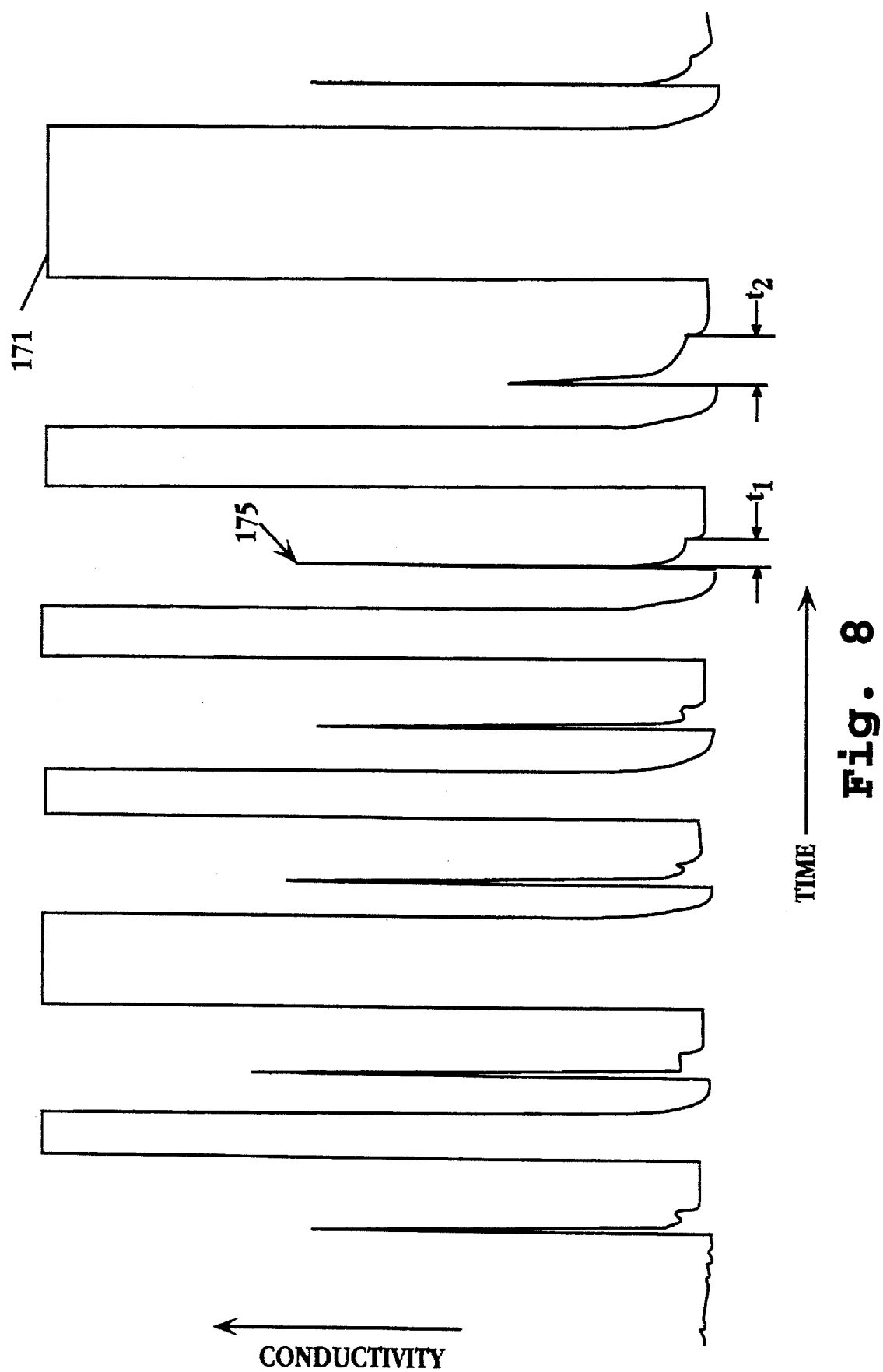
FIG. 8 is a reproduction of a trace from a strip chart recorder of conductivity of deprotection reagents in a synthesizer according to the invention.

FIG. 8 is a reproduction of strip chart records of several cycles performed with the synthesis apparatus of the invention. The drawing of FIG. 8 is not the actual strip chart record, but an artist's rendition of an actual record.

The sections of the record showing straight horizontal lines at maximum amplitude, such as portion 171, are recorded during the coupling portion of the cycle when the fluid flowing through the conductivity cell is quite conductive. The reason for the flat profile is that the needle of the strip chart recorder is at maximum deflection.

A deprotection cycle is characterized by a spike such as spike 173, which peaks rapidly and falls nearly as rapidly. Of interest in the record of conductivity for a deprotection is the slope ($\Delta$) of the curve of falling conductivity, and the time required for the slope to reach substantially zero. When $\Delta$=substantially zero the deprotection is complete and the next step in the cycle may commence. The height of the conductivity spike for a deprotection, and more importantly the time for $\Delta$ to reach substantially 0 are significant for a following coupling reaction.

It is believed that slow deprotection, typically characterized by low peak conductivity and increased time for conductivity to reach substantially a constant value is a function of a phenomenon related to exposure of the growing peptide chain to other growing peptide chains in the solid support matrix. A plausible explanation for the phenomenon is that the growing peptide chains associate with one another to increase the effective degree of crosslinking in the resin. This has the effect of reducing the diffusion rate into and out of the resin beads. The phenomenon has also been observed with UV absorbance monitoring.

In any case, an association has been observed between a "slow" deprotection and the next coupling reaction, which is most often slowed as well. The explanation of the resin adopting a less accessible state is reasonable, and could explain the effect on the following coupling reaction. The inventors believe that it is not necessary to monitor coupling if the immediately preceding deprotection is carefully monitored, which indicates the state of the resin.

In an embodiment of the present invention the $\Delta$ value is monitored and used as a signal to end a deprotection when $\Delta$=substantially zero. The next operation is then commenced. This control mechanism is also used to initiate a next step after washing operations. The time is recorded for a deprotection step from a preselected time after the step commences until $\Delta$=substantially zero, and is used to set the length of time allotted to the immediately following coupling reaction. The purpose of the preselected time period is to be sure the conductivity trace has peaked and is falling, as the peak value is also a point where $\Delta$=zero.

In FIG. 8 time $t_1$ is the measured time for one deprotection, and time $t_2$ is the time for another. It is apparent that $t_2$ is considerably longer than $t_1$ and represents a considerably slower deprotection. In a preferred embodiment of the invention the measured time for a deprotection is multiplied by four, and the result used by the controller as the time for the following coupling reaction. The multiple or other relationship between the two times can be set up by the user, and improved empirically over time.

It will be apparent to a person with skill in the art that there are many changes in the embodiments described that might be made without departing from the spirit and scope of the invention. For example, there are a number of available solenoid operable valve blocks that may be used, and there are alternative ways that a controller and associated electronics may be arranged to accomplish control requirements according to the invention. There are a broad variety of synthesis protocols that may be accomplished, and the subunit sequence is not limiting to the invention. Similarly, although the preferred embodiment is a system with relatively few (30 of so) positions for subunit cartridges, it It is claimed:

1. An automated method for solid-phase synthesis of a biopolymer by a sequential addition of a biopolymer subunit to a growing biopolymer chain carried on a solid-phase support, comprising:

placing in a position for fluid transfer, a subunit delivery cartridge having means defining a chamber and port means through which liquid can be introduced into and removed from the chamber, said chamber containing a polymer composition composed of a dried polymer substrate which is swellable in an organic solvent and which has an internal polymer matrix through which molecules of such biopolymer subunit can diffuse when the matrix is a swollen state, and molecules of said biopolymer subunit entrapped within the matrix, such that suspension of the substrate in the organic solvent produces swelling of the substrate and diffusion of said molecules of said biopolymer subunit through the matrix and into the organic solvent, and means for retaining said substrate within the chamber, where the biopolymer subunit is selected from the group consisting of an N-protected amino acid, an activated amino acid, and an activated 5'-protected nucleotide;

adding an organic solvent into said cartridge chamber through said port means, thereby causing the polymer substrate in the cartridge chamber to swell and release said biopolymer subunit into the solvent to form a solution of the subunit; and transferring the solution of biopolymer subunit into a reaction vessel containing such growing polymer chain on the solid-phase support.

2. The method of claim 1, which further includes repeating said placing, adding, and transferring steps with each of a series of cartridges containing a selected polymer subunit.

3. The method of claim 1, wherein said adding includes engaging the port means of said cartridge with fitting means for forming a fluid tight seal about said port means, supplying said organic solvent into the cartridge chamber through said port means, and removing said biopolymer subunit solution from the cartridge chamber through said port means.

4. The method of claim 3, wherein said port means includes an opening at each opposite end of the cartridge, and said fitting means includes fittings which are engageable with the cartridge openings, and movable between positions of engagement and non-engagement with the cartridge openings.

5. An automated system for solid-phase synthesis of a biopolymer by a sequential addition of a biopolymer subunit to a growing biopolymer chain carried on a solid-phase support, comprising:

a plurality of polymer-subunit delivery cartridges, each having means defining a chamber having opposite ends and port means communicating with the chamber, said chamber containing a polymer composition composed of a dried polymer substrate which is swellable in an organic solvent and which has an internal polymer matrix through which molecules of such biopolymer subunit can diffuse when the matrix is in a swollen state, and molecules of a selected biopolymer subunit entrapped within the matrix, such that suspension of the substrate in the organic solvent produces swelling of the substrate and diffusion of said molecules of the biopolymer subunit through the matrix and into the organic solvent, and means for retaining said substrate within the chamber, where the biopolymer subunit is selected from the group consisting of an N-protected amino acid, an activated amino acid, and an activated 5'-protected nucleotide; and an automated synthesis apparatus comprising
(i) a cartridge holder adapted to hold a plurality of such cartridges;
(ii) fitting means movable to a loading position effective to engage the port means of a selected cartridge in the holder, forming a fluid-tight seal with said port means,
(iii) moving means for placing a selected cartridge in said holder to said position at which the fitting means is engageable with the port means of the selected cartridge,
(iv) a reaction vessel for containing such solid-phase support, and
(v) fluid-transfer means for transferring such organic solvent into the chamber of such a selected cartridge, and for transferring such solution out of the chamber and into the reaction vessel.

6. The system of claim 5, wherein the port means in each cartridge includes an opening at each end of the cartridge, and said fitting means includes fittings movable to a position at which opposite-end openings of the cartridge are engaged in a fluid-tight fashion.

7. The system of claim 5, wherein said holder is a carousel having openings for accepting and supporting said cartridges, and said moving means includes means for rotating the carousel to place cartridges held in the carousel successively to said loading position.

8. The system of claim 5, wherein said fluid transfer means includes a first fluid vessel connected to a first fluid conduit leading to said reaction vessel and a second fluid vessel connected to a second fluid conduit leading to said reaction vessel, said second fluid vessel being connected by a third fluid conduit through a valve to said first fluid vessel, said fluid vessels capable of being individually pressurized and vented, and wherein a biopolymer subunit-carrying fluid delivered to said first fluid vessel is transferred through said reaction vessel by pressurizing said first fluid vessel with the other fluid vessel vented.

9. A method for transferring a subunit-carrying fluid through a reaction vessel containing a growing biopolymer chain on a solid-phase support in an apparatus for synthesizing a biopolymer by sequential addition of activated biopolymer subunits, comprising:

placing said solid-phase support with said growing biopolymer chain in a reaction vessel connected by a first fluid conduit to a first pressurizable pumping vessel and by a second fluid conduit to a second pressurizable pumping vessel, said first and said second pumping vessels connected through a valve by a third fluid conduit;

introducing said subunit-carrying fluid to said first pumping vessel;

closing the valve in said third fluid conduit between said first and second pumping vessels; and pressurizing said first pumping vessel, causing said subunit-carrying fluid to flow through said reaction vessel and into said second pumping vessel.

10. The method of claim 9 further comprising steps of:

opening said valve in said third fluid conduit with said subunit carrying fluid in said second pumping vessel;

venting said first pumping vessel; pressurizing said second pumping vessel, causing said subunit-carrying fluid to flow through said third conduit from said second pumping vessel to said first pumping vessel; and repeating the sequence of steps to cause said subunit-carrying fluid to flow through said reaction vessel and into said second pumping vessel.

11. An automated apparatus for solid-phase synthesis of a polypeptide by sequential addition of selected protected amino acid subunits to a growing polypeptide chain carried in a solid-phase support, comprising:

reaction vessel means for containing said solid-phase support carrying said growing polymer chain, said reaction vessel means having ports for connecting to fluid conduits;

electrically controllable fluid transfer means including fluid conduits connected to said ports of said reaction vessel such that fluid may be transferred by said fluid transfer means through said reaction vessel;

subunit delivery means connected through a first solenoid operable valve to said fluid transfer means for delivering selected amino acid subunit-carrying fluids to said fluid transfer means;

reagent delivery means connected through a second solenoid operable valve to said fluid transfer means for delivering deprotection reagent fluid to said fluid transfer means;

conductivity measuring means including a conductivity cell in said reaction vessel means; and microprocessor-based control means coupled to said solenoid operable valves, to said fluid transfer means, and to said conductivity monitoring means;

said control means being effective to control sequencing operations of said automated apparatus to alternately circulate selected protected subunit-carrying fluid and deprotection reagents through said reaction vessel means to sequentially synthesize a polypeptide, said control means monitoring conductivity of said deprotection reagent fluid, determining the rate of change of the conductivity with respect to time, measuring the total time for the rate of change of conductivity to reach substantially zero beginning from a preselected time after the deprotection step has commenced and conductivity has reached a maximum value and has begun to decrease, terminating circulation of deprotection reagent fluid when the change in conductivity with respect to time reaches approximately zero, and adjusting the total time for the next circulation of subunit-carrying fluid through said reaction vessel means to be a preset multiple of the measured time.

12. A method for determining the time to be allotted to a coupling cycle in a system for synthesizing a polypeptide by sequential addition of selected protected amino acid subunits to a growing polypeptide chain carried in a solid-phase support, said synthesizing involving alternate coupling and deprotection cycles, comprising:

measuring the decreasing conductivity of deprotection reagents applied to said solid-phase support during each said deprotection cycle by monitoring a conductivity cell placed in a conduit leaving the reaction vessel;

measuring the length of time in each said deprotection cycle from a preselected time after the deprotection step has commenced and a maximum conductivity has been detected, until the change of conductivity with respect to time equals approximately zero;

multiplying said measured length of time by a preset multiplier to obtain a calculated length of time; and adjusting the time for an immediately following coupling cycle to said calculated length of time by microprocessor control means.

* * * * *